United States Patent [19]

De Jonckheere et al.

[11] Patent Number: 4,760,764
[45] Date of Patent: Aug. 2, 1988

[54] PROCESS FOR THE CONTINUOUS MANUFACTURE HOUR GLASS-SHAPED PADS

[75] Inventors: Raphael De Jonckheere, Bondues; Jean L. Rousseau, La Croix, both of France

[73] Assignee: Boussac Saint Freres B.S.F., Lille, France

[21] Appl. No.: 900,658

[22] Filed: Aug. 26, 1986

[30] Foreign Application Priority Data

Aug. 27, 1985 [FR] France .................. 8512807

[51] Int. Cl.⁴ .............................. B26D 7/32
[52] U.S. Cl. ........................... 83/23; 83/27; 83/29; 83/46; 83/161; 156/259; 156/264
[58] Field of Search .............. 83/46, 23, 29, 27, 47, 83/112, 161; 156/259, 260, 264, 265, 512, 522; 604/385

[56] References Cited

PUBLICATIONS

WO-A-8 303 051 (Beghin-Say), p. 2, Lines 31-38, p. 3, Lines 1-21, p. 8, Lines 1-11, 24-38; p. 9, entirely; Revedications 1 to 14; FIGS. 9-15.

*Primary Examiner*—Donald R. Schran
*Attorney, Agent, or Firm*—Armstrong, Nikaido, Marmelstein & Kubovcik

[57] ABSTRACT

A method for manufacturing egg timer-shaped absorbent pads in which an absorbent material continuous strip of uniform thickness and uniform width is feed along a longitudinal path and divided in the longitudinal direction, along a continuous wavy cutting line extending symmetrically relative to the median line of the strip, into two partial strips of periodically variable width having one straight edge on and opposite wavy edge, and are offset relative to each other and superimposed, one on the other, to form a composite strip having opposite hourglass-shaped edges and a central part having a thickness twice that of the opposite edges and cutting such superimposed, composite strip in the transverse direction in the zones of maximum width.

4 Claims, 2 Drawing Sheets

PROCESS FOR THE CONTINUOUS MANUFACTURE HOUR GLASS-SHAPED PADS

The present invention relates to an egg timer-shaped absorbent pad, i.e. having a rectangular general shape with two opposite lateral indentations, for a pair of nappy-pants, as well as to a process for the continuous manufacture of such pads.

The egg timer-shaped absorbent pads comprise, in the direction of the length of the pad, two end zones and a between-the-legs intermediate zone of width smaller than that of the end zones. For reasons of effectiveness, it is desirable that these pads have, in the direction of the width, at least in the between-the-legs zone, a central part of thickness greater than that of the lateral parts.

Two embodiments of absorbent pads of this type are known.

According to a first embodiment, a pad consists of a rectangular section of a strip of absorbent material, in each of the two opposite lateral edges of which two incisions are made, the area demarcated between these two incisions being folded back in the direction of the opposite lateral edge, so that the two opposite flaps form a double thickness in the between-the-legs zone of the pad. This folding back does present problems for the high rates of production. Moreover, this folding back must be carried out with a high degree of precision so that the free edges of the opposite flaps are contiguous. In fact, if this is not the case, these edges may either be spaced apart from each other, or overlap, which modifies the function of the absorbent pad as well as the appearance of the nappy-pants.

According to another known embodiment, an absorbent pad is formed by the superimposition of a rectangular section of absorbent material, which has a width smaller than or equal to the between-the-legs width of the complete absorbent pad, on an egg timer-shaped strip of absorbent material. For the continuous manufacture of such pads, a strip of absorbent material is cut out along a rectilinear longitudinal cutting line into a relatively narrow first partial strip and a wider second partial strip, opposite and equal indentations are then cut in this wider partial strip and the narrower partial strip is placed on the wider partial strip before cutting the composite strip in the transverse direction within the areas contained between successive indentations. The main disadvantage of this process lies in the waste due to the cuts made in the wider partial strip in order to obtain the indentations.

The subject of the present invention is an egg timer-shaped absorbent pad which can be manufactured in a simple way, at a fast rate, without any waste, with an increased thickness in the median pad of the pad, especially in the between-the-legs zone.

The invention also relates to a particularly simple and rapid process for the manufacture of such absorbent pads.

The egg timer-shaped absorbent pad according to the invention, with two opposite lateral indentations, for a pair of nappy-pants, comprises, in the direction of its length, two end zones and a between-the-legs intermediate zone of width lower than that of the end zones. The pad consists of two superimposed pad parts with shapes such that the pad has, in the direction of the width, a median part of thickness greater than that of the lateral parts. According to the invention, the pad consists of two identical pad parts each having the same length as the pad and a width smaller than the width of the pad in the end zones. One of the longitudinal edges of each part of the pad is rectilinear and the other has an indentation identical to the indentations of the pad. The two parts of the pad are partially superimposed, in the inverse position, in the form of a composite pad so that their rectilinear edges overlap and their edges equipped with an indentation are situated on the opposite longitudinal sides of the composite pad.

According to one embodiment of the invention, the two pad parts overlap over a width corresponding to the width of each part of the pad at the place of its indentation. In this case, the composite pad has a double thickness over the entire width of the between-the-legs zone.

According to another embodiment of the invention, the two pad parts overlap over a width lower than the width of each pad part at the place of its indentation. In this case, the composite pad has a double thickness over only a part of the width of the between-the-legs zone, which part is situated in the middle of the width of the between-the-legs zone.

For the continuous manufacture of such absorbent pads, starting from an absorbent material in the form of a strip, the strip is continuously divided, in the longitudinal direction, into two partial strips along a wavy cutting line symmetrical relative to the median longitudinal line of the strip. The period of the wavy cutting line corresponds to the length of an absorbent pad to be manufactured. One of the partial strips thus obtained is offset relative to the other partial strip in the transverse direction over the other partial strip by a value greater than the minimum width of each partial strip, and in the longitudinal direction by a value equal to $\frac{1}{2}$, $1\frac{1}{2}$ and $2\frac{1}{2}$ periods of the wavy cutting line, so as to obtain a composite strip of which the two lateral edges are wavy in a symmetrical fashion and of which the median part has a thickness twice that of the lateral part. Finally, the composite strip is cut, at intervals corresponding to one period of the wavy cutting line, in the transverse direction in the maximum width zones of the composite strip.

It is possible to divide the strip by a sinusoidal cutting line or by a trapezoidal wave cutting line formed by an alternation of longitudinal straight line segments of identical length, situated in the transverse direction at an equal distance on either side of the median longitudinal line of the strip, and of the inverted transverse segments joining the said straight line segments to one another.

According to a preferred embodiment, one of the partial strips is offset in the transverse direction and in the longitudinal direction relative to the other partial strip by making it describe a loop around a roller of which the axis is situated in a plane parallel to the plane of the strip, above or below the latter, and is inclined relative to the transverse direction of the strip.

It is possible to offset one of the partial strips in the transverse direction relative to the other partial strip by a value less than, equal to or greater than the maximum width of the partial strip.

An illustrative and nonlimiting embodiment of the subject of the invention will be described hereinafter, in greater detail, referring to the diagrammatic drawings attached; on the drawings.

Figure 1:
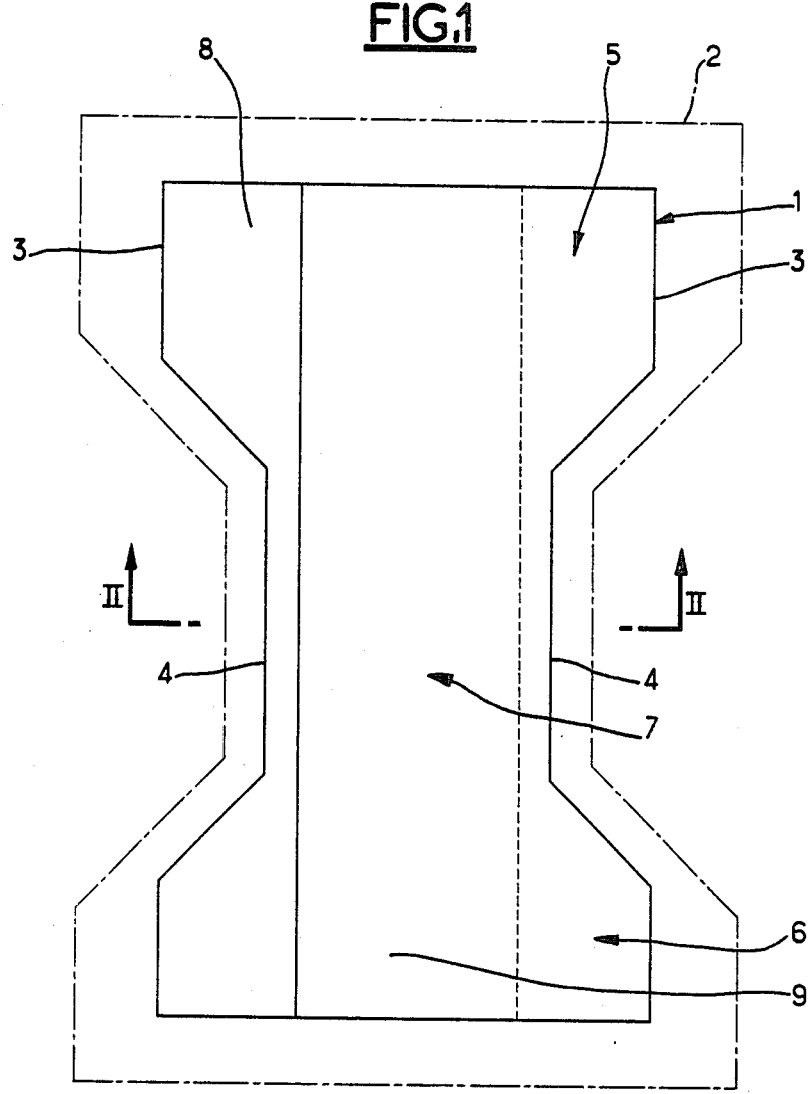
FIG. 1 is a overview of a composite absorbent pad according to the invention.
Figure 2:
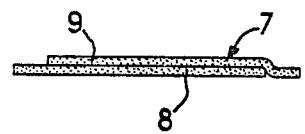
FIG. 2 is a section along II—II of FIG. 1.

According to FIGS. 1 and 2, an absorbent pad 1 intended to be incorporated into a pair of nappy-pants 2 of which only the contour is indicated by dot-and-dash lines on FIG. 1, has, as does the pair of nappy-pants 2, the shape of an egg timer, known per se. This egg-timer shape is due to the presence, along each of the two opposite longitudinal edges 3 of the pad 1, of a cut 4 in the shape of a trapezoidal indentation. The absorbent pad 1 thus comprises a rear end part 5, a front end part 6 and a between-the-legs intermediate part 7 situated between the two indentations 4. It is recognised from FIG. 1 that the rear end part 5 may, in a way known per se, be somewhat higher than the front end part 6. For fastening the nappy-pants, the rear end part 5 may, in a known way, be provided with adhesive fasteners, which are not shown.

The absorbent pad 1 consists of two identical pad parts 8,9. Each part 8,9 has a rectangular general shape, with an indentation 4 along one of the longitudinal edges, whereas the other longitudinal edge is rectilinear. The width of each pad part 8,9, at the place of the indentation 4, is lower than the width of the pad 1 in the between-the-legs zone 7. The two pad parts 8,9 are partially superimposed, in the inverted position, so that their rectilinear longitudinal edges overlap and their longitudinal edges equipped with an indentation 4 are situated on the opposite sides of the composite pad 1.

Thus, as can be seen especially from FIG. 2, the composite pad has, over its entire length, on either side of a double thickness median strip, of a width smaller than the width of the between-the-legs zone 7, a single-thickness strip which has a low width in the between-the-legs zone 7 and an increased width in the two end zones 5 and 6.

Figure 3:
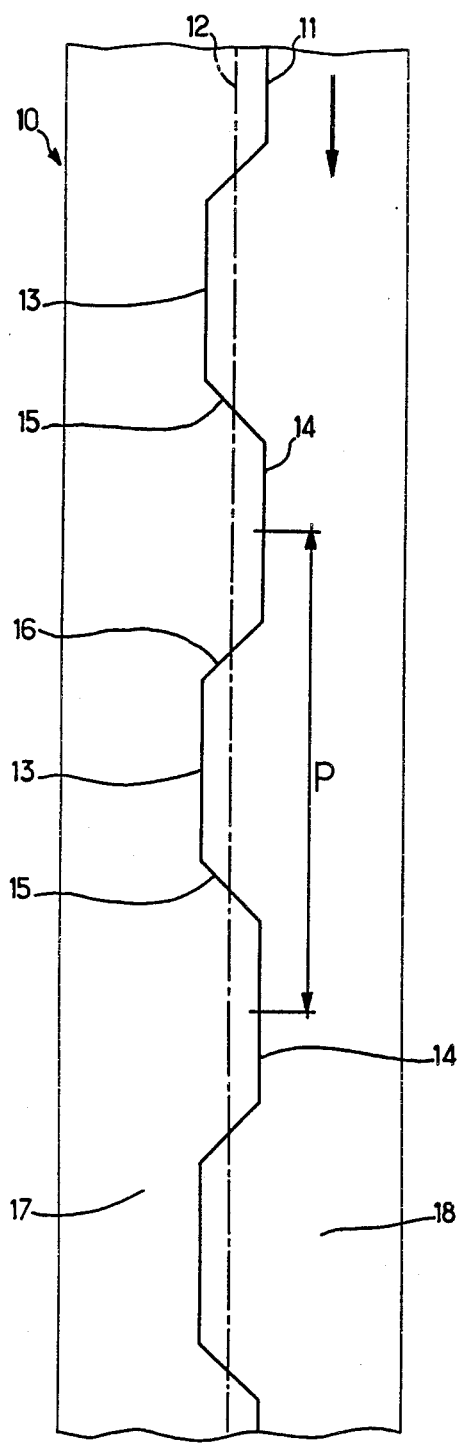
FIG. 3 represents a section of absorbent material, divided along a wavy cutting line.

For the continuous manufacture of absorbent pads according to FIGS. 1 and 2, a strip 10 of absorbent material is continuously divided, according to FIG. 3, in the course of unwinding the strip, in the longitudinal direction of the latter, along a wavy cutting line 11 symmetrical in relation to the median longitudinal line 12 of the strip. The wavy cutting line 11 is a trapezoidal wave line formed from an alternation of longitudinal straight line segments 13 and 14, of identical length, situated at equal distance on either side of the median line 12, and of the inverted, oblique straight line segments 15 and 16, joining the straight line segments 13 and 14 to one another. The period p of the wavy cutting line 11 is chosen so that it corresponds to the length of an absorbent pad to be manufactured.

The strip 10, of which the width is greater than the width of the absorbent pad to be manufactured, is thus divided without waste by the wavy cutting line 11 into two complementary partial strips 17, 18, each having a rectilinear longitudinal edge and a wavy longitudinal edge.

Figure 4:
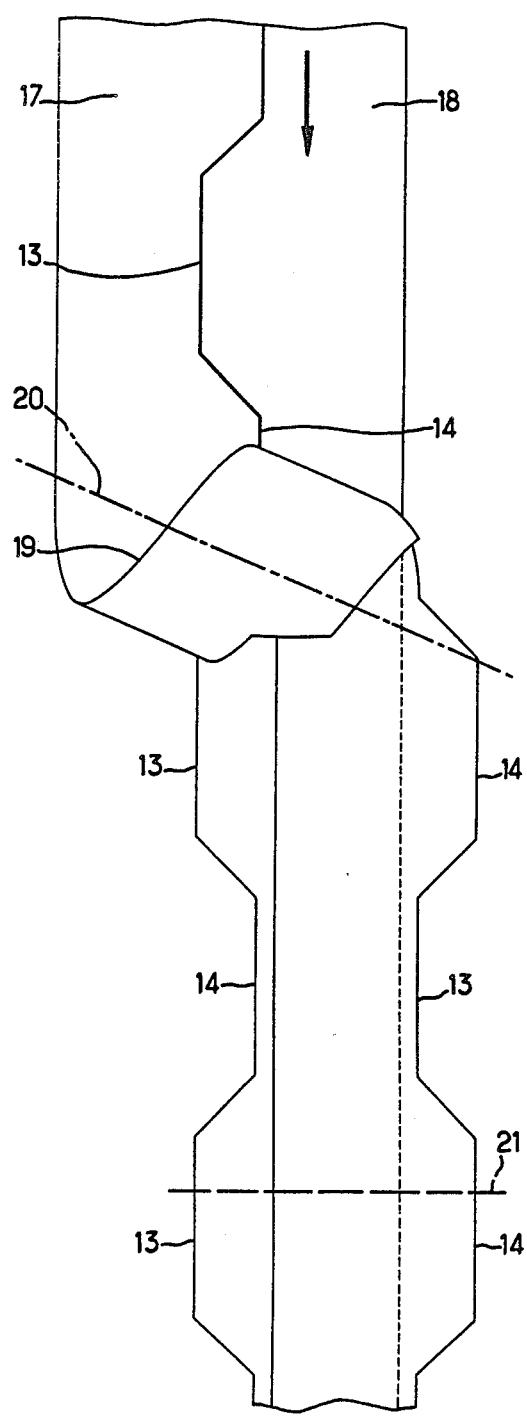
FIG. 4 illustrates the offsetting in the transverse and the longitudinal directions of one of the two partial strips relative to the other, in order to change the strip of FIG. 3 into the form of a composite strip which is ready to be cut out in the transverse direction into absorbent pads.

According to FIG. 4, the partial strip 17 is made to travel, while the partial strip follows its rectilinear path, in the shape of a loop 19 around a roller, not shown, of which the axis 20 is contained in a plane parallel to the plane of the strips 17, 18, at a distance above this plane. The axis 20 is inclined relative to the length of the strips 17, 18, so that the passage in the form of a loop 19 of the strip 17 around the roller causes a lateral offsetting of the strip 17 in the direction of the strip 18, at the same time as a longitudinal offsetting by one and a half periods relative to the strip 18. Following the loop 19, the partial strip 17 is thus partially superimposed on the strip 18, so that the wavy longitudinal edge of each partial strip 17, 18 extend in the lateral direction beyond the rectilinear longitudinal edge of the other partial strip 18, 19. A composite strip having a double-thickness in its median part and, on either side of this double thickness median part, single thickness parts with symmetrically wavy outer edges, is thereby obtained.

In order to obtain individual absorbent pads from such a composite strip, it suffices to cut the strip in the transverse direction, opposite each zone of increased width, at intervals corresponding to the period p, as shown at 21 on FIG. 4. It is noticed that the transverse cut 21 does not pass through the middle of the zones of increased width of the composite band, which enables pads with end zones of different heights to be obtained, as shown in FIG. 1.

It goes without saying that the embodiment described above and illustrated with the Figures attached, has been given only by way of nonlimiting example and that many modifications and variations are possible within the scope of the invention.

Thus, the strip 10 could also be cut along a sinusoidal wavy line, in which case the absorbent pad would have curvilinear longitudinal edges. Furthermore, the longitudinal offsetting of one of the partial strips relative to the other, by the formation of a loop 19, could also correspond to half a period or two and a half periods, etc. Finally, the offsetting in the transverse direction of one of the partial strips relative to the other, in order to obtain a superimposition of the two strips, could also be of a smaller magnitude than according to FIG. 4, in which case, the entire between-the-legs zone could be of double thickness, or of a greater magnitude, in which case, the overlapping width of the two pad parts would be lower.

The absorbent pad according to the invention may be manufactured using any absorbent material in the form of a strip, for example cellulose wadding ("fluff") with or without superabsorbent material incorporated and with or without lining materials such a paper, etc.

We claim:

1. A method for continuous manufacture of hourglass-shaped absorbent pads from an absorbent material in the form of a initial continuous strip of uniform thickness and uniform width, having two parallel straight longitudinal edges, comprising continuously feeding said initial strip in a longitudinal path and, while feeding said initial strip in said longitudinal path, continuously dividing said strip in the longitudinal direction along a continuous wavy cutting line extending symmetrically relative to the longitudinal median line of said strip and periodically intersecting said longitudinal median line, the period of said wavy cutting line corresponding to the length of an absorbent pad to be manufacturing, into two partial strips of periodically variable width each having one straight longitudinal side edge defined by one of said side edges of the said initial strip and one opposite wavy longitudinal side edge defined by the said wavy cutting line, continuously offsetting the partial strips relative to each other in the transverse direction of the initial strip by a distance at least as great as the minimum width of each said partial strip so as to superpose the said partial strips one on the other, and in the longtudinal direction of the initial strip by a distance equal to ½, 1½, 2½, etc. periods of the said wavy cutting line, to obtain a composite strip the two longitudinal side edges of which corresponding to the said wavy longtudinal side edges of said partial strips are wavy in a symmetrical fashion, the said composite strip having a continuous central part defined between the said straight side edges of said two superposed partial strips, and two lateral parts defined between the said wavy side edges of said two superimposed partial strips, the said continuous central part having a thickness twice that of said lateral parts, and successively cutting the said composite strip at intervals corresponding to one period of said wavy cutting line, in the transverse direction in the zones of maximum width of said composite strip, into discrete hourglass-shaped absorbent pads.

2. A method according to claim 1, wherein said continuous initial strip is continuously divided in said longitudinal direction along a trapezoidal wave cutting line formed by two series of longitudinal straight line segments, of identical length, situated at equal distance alternately sides of the median longitudinal line of said strip, and by a series of alternate oblique straight line segments joining the said opposite longitudinal straight line segments to one another.

3. A method according to claim 1 or 2, wherein one of said partial strips is offset relative to the other of said partial strips in the transverse and longitudinal directions by passing said one of said partial strips through a loop around a roller having its axis situated in a plane parallel to the plane of said strip, above or below said plane of the latter, and said axis is inclined relative to the transverse direction of the strip.

4. A method according to claim 1, wherein one of said partial strips is offset in the transverse direction relative to the other of said partial strips by a distance at least equal to the maximum width of each of said partial strips.

* * * * *